(12) United States Patent
Eli

(10) Patent No.: US 8,372,215 B2
(45) Date of Patent: Feb. 12, 2013

(54) HUMAN-INTERFACE CLEANING DEVICE

(76) Inventor: Bradley A. Eli, Encinitas, CA (US)

(*) Notice: Subject to any disclaimer, the term of this patent is extended or adjusted under 35 U.S.C. 154(b) by 575 days.

(21) Appl. No.: 12/709,469

(22) Filed: Feb. 20, 2010

(65) Prior Publication Data
US 2010/0175726 A1  Jul. 15, 2010

Related U.S. Application Data

(63) Continuation-in-part of application No. 11/751,461, filed on May 21, 2007, now abandoned.

(51) Int. Cl.
B08B 9/032 (2006.01)

(52) U.S. Cl. ............. 134/166 C; 134/137; 134/166 R

(58) Field of Classification Search .......... None
See application file for complete search history.

(56) References Cited

U.S. PATENT DOCUMENTS

| | | |
|---|---|---|
| 3,568,678 A | 3/1971 | Pourquier et al. |
| 4,424,833 A | 1/1984 | Spector et al. |
| 5,300,032 A | 4/1994 | Hibbs et al. |
| 5,630,795 A | 5/1997 | Kuramoto et al. |
| 5,664,594 A | 9/1997 | Kee |
| 6,082,361 A | 7/2000 | Morejon |
| 6,602,219 B2 | 8/2003 | Madesen |
| 6,805,125 B1 | 10/2004 | Crump |

Primary Examiner — Michael Kornakov
Assistant Examiner — Ryan Coleman
(74) Attorney, Agent, or Firm — Eric A. Hanscom; Todd J. Langford

(57) ABSTRACT

A human-interface cleaning device for cleaning human-interface devices commonly used for the treatment sleep apnea. The cleaning device has a solvent-receiving end which connects to a solvent-delivery source such as a faucet or shower head. At the opposite end of the cleaning device is a funnel-like shaped solvent-discharge end which is tapered at its distal end and adapted to easily friction-fit into any receiving aperture of most human-interface devices. The inner chamber of the device has one or more fins each having an angled flap at their ends. As so connected to a solvent-delivery source and to a human-interface device, the cleaning device will enhance the force of the solvent being delivered through the cleaning device and more easily and effectively clean the human-interface device to which attached.

10 Claims, 2 Drawing Sheets

HUMAN-INTERFACE CLEANING DEVICE

CROSS REFERENCES TO RELATED APPLICATIONS

This application is a continuation-in-part of my application, Ser. No. 11/751,461 filed on May 21, 2007 now abandoned. This application is hereby incorporated by reference into this application.

STATEMENT REGARDING FEDERALLY-SPONSORED RESEARCH OR DEVELOPMENT

None.

BACKGROUND

This device of this disclosure relates to an improvement in cleaning devices for tube-like objects and systems, and more particularly to a cleaning device suited for cleaning and maintaining tube-like components use in and for respiratory systems, Sleep apnea is a true breathing obstruction which, according to the National Institutes of Health, affects over 12 million Americans. A person afflicted with sleep apnea requires that person, when sleeping, to awaken to begin breathing again. Snoring is a common symptom of sleep apnea, a result of the obstruction, and sometimes even a cause of sleep apnea. Snoring by itself, however, does not involve the cessation of breathing.

As concisely stated by the National Sleep Foundation on their website and included herein, sleep apnea causes a person to stop breathing periodically throughout sleep, which upsets the balance of oxygen and carbon dioxide in the blood. The brain senses the reduction in oxygen and the increase in carbon dioxide and sends a signal to resume breathing. The person wakes up in response to the breathing arousal signal from the brain. The muscles of the tongue and throat awaken to enlarge the airway and allow carbon dioxide to escape and oxygen to enter. The waking episodes are necessary to restart breathing (and save the person's life), but they prevent the individual from getting high-quality sleep.

On a physical level, the sleep apnea sufferer cannot breathe because they have an obstructed airway. The throat muscles and tongue relax too much and may be enlarged or misshapen, so the air passage is narrowed during sleep.

Sleep apnea sufferers awaken frequently to restart breathing, but they remember little or nothing of being awake. Frequent waking at night may be a sign of sleep apnea. The frequency of waking episodes varies, but may be between 10 and 60 per night. Severe sleep apnea may cause the sleeper to experience more than 100 waking episodes in a single night. One measure of sleep apnea is that the person must stop breathing for a period of at least 10 seconds or more, five times within an hour. Some sleep apnea sufferers may stop breathing for as long as two minutes. Basically there are three types of sleep apnea; obstructive sleep apnea, central sleep apnea, and mixed sleep apnea.

Obstructive Sleep Apnea (OSA) is the most common type of sleep apnea. OSA is caused by an obstruction in or blockage of the airway usually when the soft tissue in the rear of the throat collapses and closes during sleep which then actually stops the air flow in the nose and mouth. Throat and abdominal breathing continue normally. Obstructive Sleep Apnea is commonly accompanied by snoring and causes the sleeper to wake up, gasping or snorting, and then go back to sleep again.

Central Sleep Apnea (CSA) is a much less common type than Obstructive Sleep Apnea. In Central Sleep Apnea, the airway is not blocked but the brain fails to signal the muscles to breathe or the brain signal that instructs the body to breathe is delayed. With CSA, oral breathing and throat and abdominal breathing all cease at the same time. The periods of breathing interruption may last a few seconds, and breathing may be too shallow to provide oxygen to the blood and tissues. CSA may be associated with irregular heartbeat, high blood pressure, heart attack, and/or stroke.

Mixed sleep apnea is a combination of the two other types of sleep apnea, Obstructive Sleep Apnea and Central Sleep Apnea, at the same time.

With each apnea event, however, the brain briefly arouses the sleeper in order for them to resume breathing. Consequently sleep is extremely fragmented and of poor quality. Despite the difference in the root cause of each type of sleep apnea, in all three, people with untreated sleep apnea stop breathing repeatedly during their sleep, sometimes hundreds of times during the night and often for a minute or even longer.

Signs and symptoms of sleep apnea include:

a. Frequent cessation of breathing (apnea) during sleep. Your sleep partner may notice repeated silences from your side of the bed.

b. Choking, gasping, or gagging during sleep to get air into the lungs c. Loud snoring d. Waking up sweating during the night e. Feeling unrefreshed in the morning after a night's sleep f. Headaches upon awakening g. Daytime sleepiness, including falling asleep at inappropriate times, such as during driving or at work h. Lethargy I. Rapid weight gain j. Memory loss and learning difficulties k. Short attention span l. Poor judgment m. Depression n. Personality changes o. Untreated sleep apnea also may be responsible for job impairment and motor vehicle crashes.

Several known causes of sleep apnea include:

a. Obstructed airway.

b. Central nervous system disorder such as a stroke, a brain tumor, or even a viral brain infection.

c. Chronic respiratory disease.

d. Obesity or excessive weight gain e. Age.

f. Gender. Men are more likely to experience sleep apnea because they have narrower airways than do women.

g. Irregular sleep hours.

h. High blood pressure is another risk factor for sleep apnea.

i. Anatomic abnormalities or facial deformities, such as nasal obstruction, an enlarged tongue, a narrow airway, a receding chin, a small jaw, tissues blocking the airway, a deviated septum, polyps, or certain palate and jaw shapes.

j. Snoring itself is not only a result of sleep apnea, but also a cause. The repeated vibrations of the soft palate during snoring can cause the soft palate to lengthen, which can obstruct the airway.

k. Enlarged tonsils or adenoids in children.

l. Use of alcohol and sedatives before bedtime.

m. Nasal congestion, nasal blockages, and nasal irritants such as household dust and dander can inhibit breathing through the nose and force breathing through the throat, which may also be blocked n. Severe heartburn or acid reflux (gastroesophageal reflux disease, or GERD).

As mentioned earlier, sleep apnea is very common and affects more than 12 million Americans. Risk factors include being male, overweight, and over the age of 40, but sleep apnea can strike anyone at any age, even children. Because of the lack of public awareness and lack of awareness by many healthcare professionals, the vast majority of those suffering from sleep apnea remain undiagnosed and therefore remain untreated, despite the fact that this serious disorder can have significant consequences.

Untreated, sleep apnea can cause high blood pressure and other cardiovascular disease, memory problems, weight gain, impotency, and headaches. Sleep apnea is a dangerous and progressive sleep disorder and it generally gets worse as the person afflicted with it ages. Not only does sleep apnea result in sleep deprivation, but it also can threaten your life.

Sleep apnea, however, can be diagnosed and it can be treated effectively. To diagnose for sleep apnea, a doctor will probably perform a physical examination of the person's mouth; and/or recommend an overnight sleep study in a sleep clinic.

Several treatment options currently exist and on-going research into additional treatment options continues. Several such treatment options include behavioral changes, surgery (extremely intrusive), medication (though not generally effective), and physical and mechanical therapy. The latter (physical and mechanical therapy) have been found most effective in the treatment of sleep apnea.

Such physical and mechanical therapies include oxygen administration, Continuous Positive Airway Pressure (CPAP), surgery, and dental appliances or jaw adjustment devices. Of these, Continuous Positive Airway Pressure (CPAP) is one of the most common long-term treatments for severe sleep apnea.

CPAP therapy requires the person to wear a mask over their nose during sleep. The mask blows air through the nasal passages, and the pressure is adjusted to keep the airway open during the night. A mask in such therapies, however, is cumbersome to use, uncomfortable to wear, especially while trying to sleep, and difficult to maintain.

A novel air passage device entails the use of a nasal interface which has nasal ports to be inserted directly into one's nostrils. This device is illustrated in FIG. 1 and has been found to be equally effective as a CPAP treatment therapy while at the same time causing little or no discomfort to the wearer as opposed to the mask described earlier.

Either form of Continuous Positive Airway Pressure is often successful in treating sleep apnea, although for to be effective, CPAP patients must consistently use the nasal mask or nasal interface and commit to other lifestyle changes as well, such as losing weight. Unfortunately, many people find CPAP a difficult treatment because of discomfort or claustrophobia as to the mask. Additionally, and the most common reason for discontinued use of CPAP, particularly for those using the nasal interface, is the required daily maintenance of the device used. Therefor, while CPAP is effective, it is often unsuccessful because of noncompliance.

The device of this present disclosure provides a solution for non-use of these important CPAP treatment systems, particularly those using the nasal interface type, by greatly simplifying the maintenance and cleaning process for these treatment systems.

The foregoing has outlined some of the more pertinent objects of the cleaning device of the present disclosure. These objects should be construed to be merely illustrative of some of the more prominent features and applications of the cleaning device of the present disclosure. Many other beneficial results can be attained by applying the disclosed cleaning device of the present disclosure in a different manner or by modifying the cleaning device of the present disclosure within the scope of the disclosure. Accordingly, other objects and a fuller understanding of the cleaning device of the present disclosure may be had by referring to the summary of the cleaning device of the present disclosure and the detailed description of the preferred embodiment in addition to the scope of the cleaning device of the present disclosure defined by the claims taken in conjunction with the accompanying drawings.

SUMMARY

The above-noted problems, among others, are overcome by the cleaning device of the present disclosure. Briefly stated, the cleaning device of the present disclosure contemplates a human-interface cleaning device having a solvent-receiving member with a flexible base and three or more slits emanating outward from at or near its center defining an opening thereat and defining three or more flexible flaps; a side wall around the base; an inner chamber with one or more forward extending fins with angled flaps at their ends; and a solvent-discharge member above the side wall wherein the solvent-discharge member tapers down to a smaller diameter and a tube-like extension resembling a funnel.

With the solvent-receiving end of this cleaning device attached to a suitable solvent-delivery source, such as, but not limited to, a faucet, and the solvent-discharge end of this cleaning device attached to a receiving aperture of a hose or other receiving aperture of a human-interface device, the funnel-like structure of the solvent-discharge end will cause the force of the solvent entering the cleaning device to be much greater than the force of the solvent entering the cleaning device such that the cleansing power of the cleaning device will be greatly enhanced.

The foregoing has outlined the more pertinent and important features of the cleaning device of the present disclosure in order that the detailed description that follows may be better understood so the present contributions to the art may be more fully appreciated. Additional features of the cleaning device of the present disclosure will be described hereinafter which form the subject of the claims. It should be appreciated by those skilled in the art that the conception and the disclosed specific embodiment may be readily utilized as a basis for modifying or designing other structures and methods for carrying out the same purposes of the cleaning device of the present disclosure. It also should be realized by those skilled in the art that such equivalent constructions and methods do not depart from the spirit and scope of the cleaning device of the present disclosure as set forth in the appended claims.

BRIEF DESCRIPTION OF THE DRAWINGS

For a fuller understanding of the nature and objects of the cleaning device of the present disclosure, reference should be had to the following detailed description taken in conjunction with the accompanying drawings in which.

DETAILED DESCRIPTION

Figure 1:
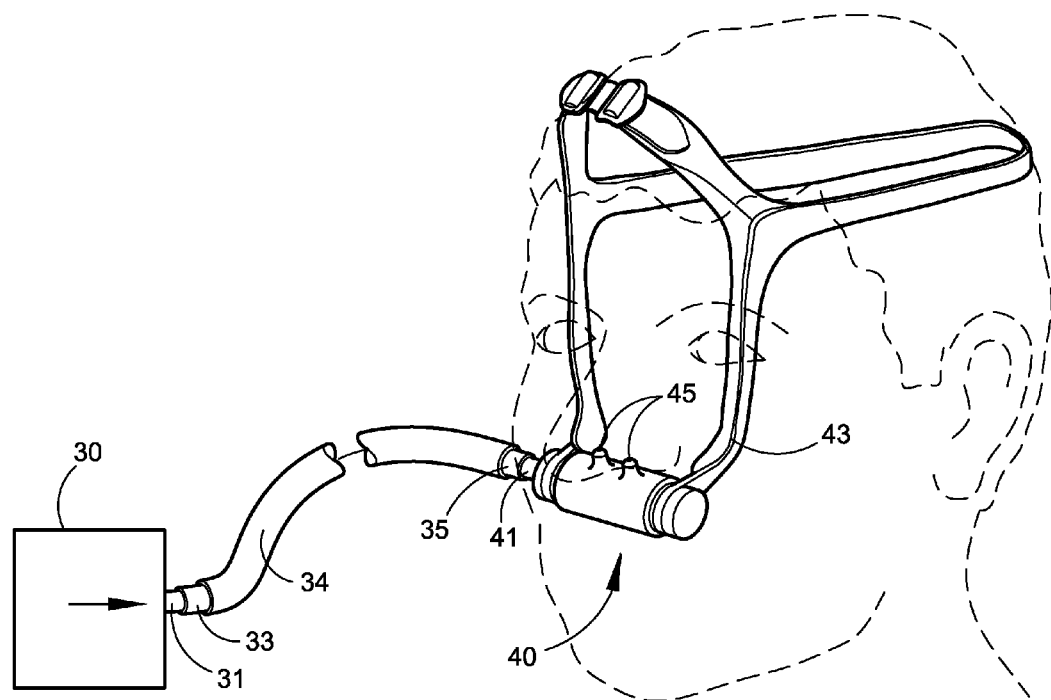
FIG. 1 is a perspective view of a human-interface system and an illustration of its use.
Figure 2:
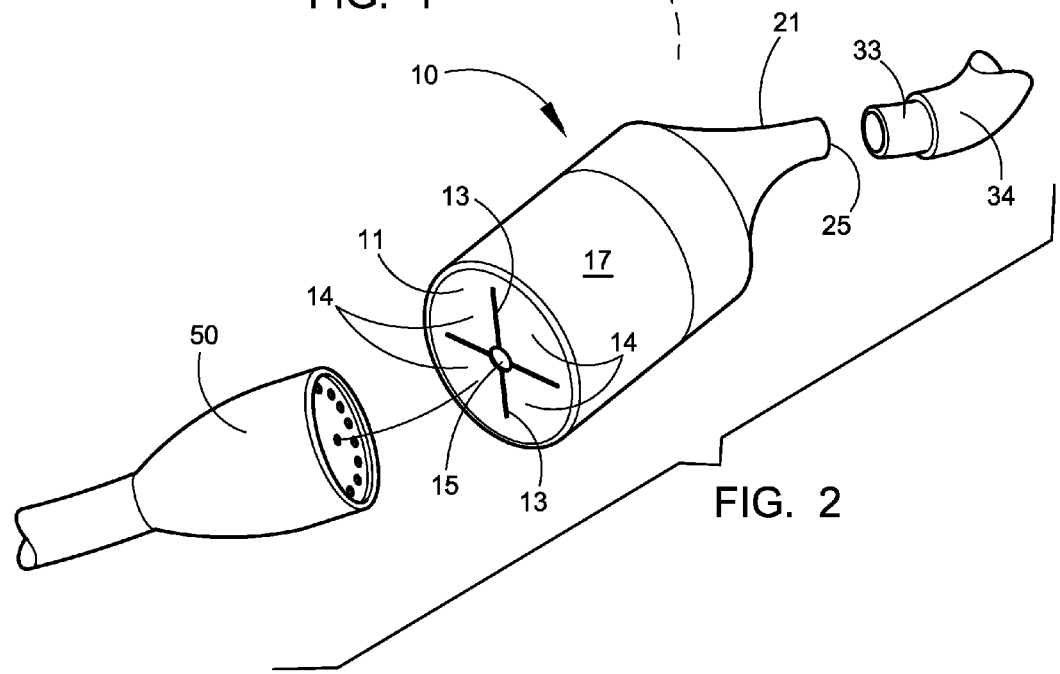
FIG. 2 is a perspective view of the cleaning device of the present disclosure.

Referring now to the drawings in detail and in particular to FIG. 2, reference character 10 generally designates a cleaning device constructed in accordance with a preferred embodiment of the cleaning device of the present disclosure. FIG. 1 illustrates the device and operations of associated with Continuous Positive Airway Pressure (CPAP) as a treatment for sleep apnea.

The device 40 typically is typically what is referred to in the art as a human-interface. It can be a full-face mask or a partial-face mask or a nasal-like device [as illustrated in FIG. 1] which has two nasal ports 45 insertable into a user's nostrils. It must be understood that the human-interface device 40 as referred to herein could be mask-like or nasal-like with nasal ports 45. In either event, the purpose of the human-interface device 40, whether mask-like or nasal-like, it to force air into the user. The cleaning device 10 of this disclosure is adapted to clean both types and is not limited to the nasal-like only.

FIG. 1 illustrates the human-interface 40 as nasal-like having nasal ports 45 which fit into one's nostrils. Attachment straps 43 on the device 40 typically fit over the user's head to hold the device 40 in place while the user sleeps. This device 40 is attached to an air-flow generator 30 via a flexible hose 34. The flexible hose 34 has attachment interfaces 33, 35 at each end. One end, the air-flow attachment interface 33, is connected to the air-flow port 31 of the air-flow generator 30. The other end, the human-interface device attachment interface 35, connects to the in-take port 41 of the nasal-interface device 40.

A person suffering from sleep apnea will don the device 40 with hose 34 attached to the device 40 and to the air-flow generator 30. The air-flow generator 30 will then be turned on which directs a continuous flow of air through the hose 34, into and through the human-interface device 40 and into the wearer's nostrils. The air pressure is adjusted to keep the airway open during the night and assist the user in breathing thereby defeating the effects of sleep apnea.

As mentioned previously, cleaning such a device 40, whether nasal-like or mask-like, is cumbersome and many people neglect this task or, in the alternative, discontinue CPAP treatment. Either option is not desirable from a healthcare perspective. The cleaning device of the present disclosure 10 solves this dilemma and simplifies the cleaning process associated with cleaning typical and similar human-interface devices 40 as described herein whether such be mask-like or nasal-like in configuration.

The cleaning device 10 of the present disclosure has a solvent-receiving member 11 [its base], a hollow inner chamber 24 forward of the base and throughout terminating at the exit opening 25. The solvent may be water, the universal solvent, or any other commercially available solvent suited for the intended purpose of conveying a solution to and through the human-interface device 40 so as to cleanse it.

The base 11 has an opening 15 with two or more axial slits 13 extending outward from the opening 15 toward the perimeter of the base 11 thereby forming the flaps 14. The opening 15 may be, but need not be, centrally located on the base. The base 11 and its flaps 14 are made of flexible material such as, but not limited to, rubber, vinyl, resilient polymers, or combinations thereof.

Figures 3, 4:
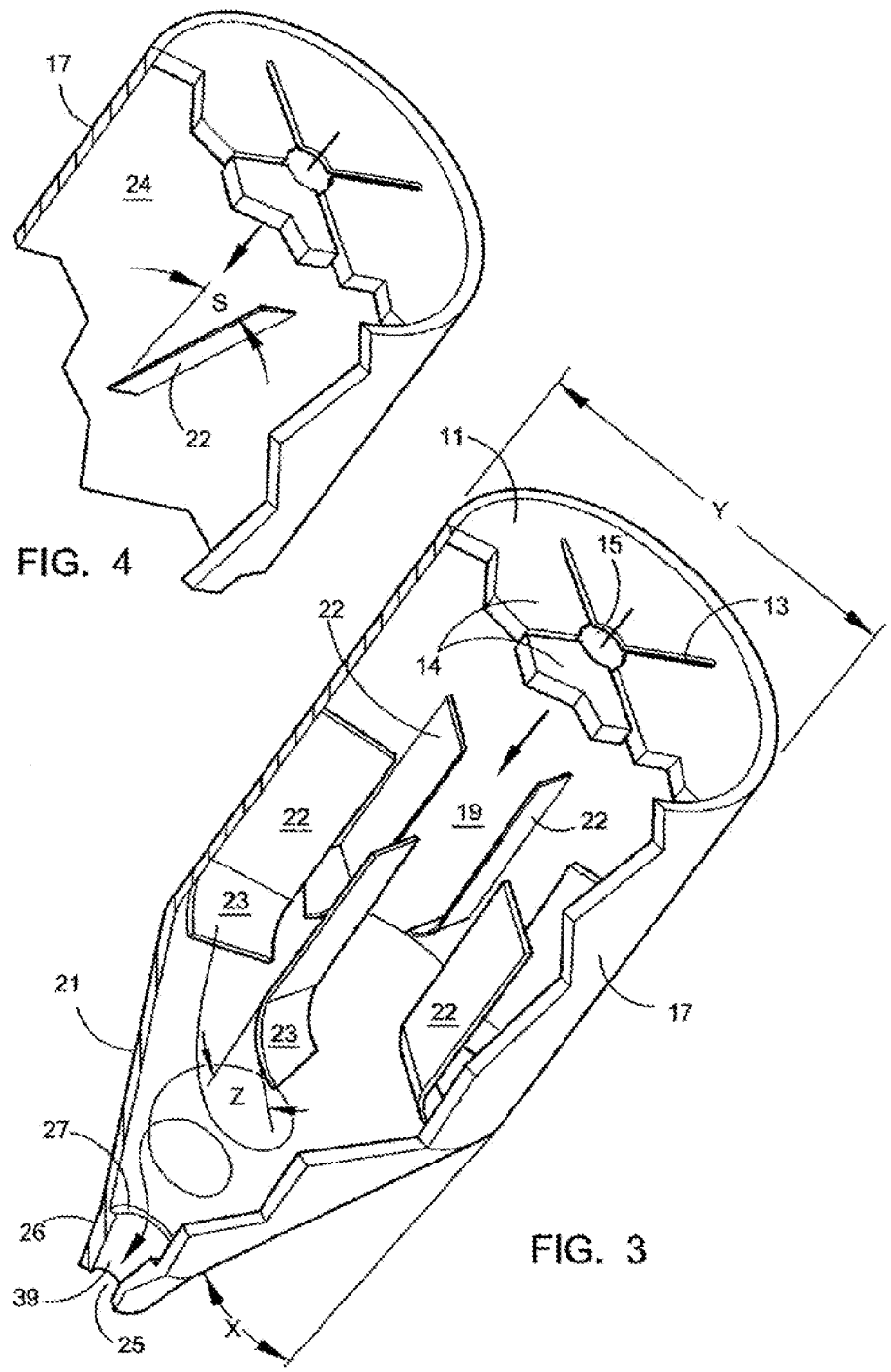
FIG. 3 is cut-away view of the internal structure of the cleaning device of the present disclosure.
FIG. 4 is a detailed view of the angled fins.

A side wall 17 extends forward of the base 11 and may be relatively straight [i.e., approximately perpendicular to the base 11] or may be angled inward to the exit opening 25. As illustrated, the side wall is relatively straight. An angling wall 21, angling inward, extends forward of the side wall 17 as seen in FIG. 3. The angle for the angling wall 21 is referred to as Angle-X. The angling wall 21 downward to the exit opening 25 resembles a cone-like structure or extension and defines an angled channel 29 therein. The angles for the angling inward and downward of this wall 21 [angle-X] ranges from approximately 30° to approximately 60°. The optimum angles for the intended purpose ranges from approximately 38° to approximately 42°.

In this illustration, the angling wall 21 comes to a step or ridge 27, followed by an tapering attachment wall 26 [tapering to permit attachment of the flexible hose 34 thereto] tapering inward to the exit opening 25 at the distal end of the device 10 and defining therein an exit channel 39. This cone-like extension of angling wall 21 with exit opening 25, with or without the tapering attachment wall 26 and exit channel 39, nearly resembles a funnel-type device. The device 10 however, need not have the ridge 27 and, if without the tapering attachment wall 26, the angling wall 21 should be angled such that it will accommodate attachment of the flexible hose 34 [dimensions of tapering/angling described below for the tapering attachment wall 26 which is structured to accommodate attachment of the flexible hose 34].

FIG. 3 illustrates the proximal end of the angling wall 21 as attached to the distal end of the side wall 17 and has a predetermined outside and inside diameter which is approximately equal to the outside and inside diameter of the side wall 17, respectively. From this point of attachment, the angling wall 21 tapers [inward angling] to a smaller outside and inside diameter which may continue to the exit opening 25 or to the step 27 as described above.

The inner walls of this inner chamber 24 are contoured similarly as the diameters described above for the side wall 17 [referred to as Diameter-Y or Y], the angled channel 29, and the exit channel 39. Consequently, as solvent is forced through the cleaning device 10, the decreasing inside diameters of the inner chamber 24, in cases where it is fully angled, or angled only from the angling wall 21 forward will create a greater force of movement of the solvent through the inner chamber 24 and, concomitantly, greater cleansing power.

For a greater force of movement of solvent, the inner chamber 24 has one or more elongated, inward extending and forward extending fins 22 [extending from near to the base 11 forward to the angling wall 21]. The fins may extend inward approximately one-eighth to one-fourth of Diameter-Y and may be perpendicular to the side wall 17 or angled. Angling may be diagonally off the sidewall 17 at approximately between 10° to approximately 30° as viewed from the axis of the inner chamber 24. This angling is referred to as Angle-S [FIG. 4 refers].

With three or more such fins 22 inside the inner chamber 24, a fin channel 19 is defined within the fins 22. The fins 22 act as channel directors to keep the solvent flowing evenly and forward without causing any undue sideward movement. The more direct the movement of solvent through the device 10, the greater the force and cleaning power of the solvent. The fins 22 may be relatively straight [as illustrated in FIG. 4] or have an angled flap 23 at the bottom toward the exit opening 25 [as illustrated in FIG. 3]. Such angling should not generally be an abrupt angle with a sharp corner of demarcation but should be a curved transition into the angling as illustrated in the respective figure.

Such an angled flap 23 will increase the force of flow of solvent. Each angled flap 23 should be angled in the same direction and such angled is referred to as Angle-Z. Angle-Z ranges from between approximately 10° to approximately not more than 45° with respect to the fin 22 to which connected. The length of the angled flap 23 should about 20% to about 35% of the total length of the fin 22/flap 23 combination.

As solvent flows through the inner chamber 24 and fin channel 19 and comes into contact with the angled flaps 23, a tornado effect is created which generates even more force of flow of the solvent.

There is a tapering attachment wall 26 extending downward from the bottom of the angling wall 21 to the exit opening 25. This tapering is important and its relative decreasing downward diameters for permitting a secure fit of the flexible hose 34 and its interface 33 thereto. Typically the outside diameter of the interface 33 of the flexible hose 34 is approximately 21 mm. The outside diameter of the tapering attachment wall 26, at is distal end [i.e., at the exit opening 25] should be less than 21 mm and the diameter increases to a diameter greater than 21 mm as the tapering attachment wall 26 reaches the bottom of the angling wall 21. Therefore the outside diameter of the tapering attachment wall 26 should range from approximately 20 mm at the exit opening 25 to approximately 22 mm at a point of adjacency to the angling wall 21.

A venturi effect is caused by this configuration which in turn accelerates the tornado effect above producing greater force of flow of solvent and, consequently, greater cleansing ability.

The downward end of the device 10 [angled cone-like extension 21, 25, 26 generally should be resilient and flexible. In this regard, the cone-like extension 21, 25, 26 and in particular, the exit opening 25, should be made of vinyl, rubber, resilient polymers, or any combinations thereof.

The tapering of the angling wall 21, the tapering attachment wall 26, and the exit opening 25, and their flexibility permits easy friction-fit insertion of the device 10 into the air-flow attachment interface 33 of the hose 34 such that the outside diameter of the exit opening 25, as it inserts into the air-flow attachment interface 33, increases in diameter until it is securely nested into the inside diameter of the air-flow attachment interface 33.

After a user of the human-interface device 40 awakens from sleep, the user will remove the device 40 and disconnect the hose 34 from the air-flow generator 30. The user will then re-connect the hose 34 directly to the tube-like extension 21, 25 of the cleaning device of the present disclosure 10. The user will then attach the base 11 to any external faucet, shower head, or similar external solvent transporting mechanism or solvent discharge mechanism. As seen in FIG. 2, a shower head 50 is illustrated. Once the cleaning device of the present disclosure 10 is attached to the human-interface device 40 and to the shower head 50 [for example], water is turned on. The water will forcibly course a path through the cleaning device of the present disclosure 10, through the hose 34, and into and through the human-interface device 40 thereby flushing out any contaminants and build-up contained therein. In this manner, both the hose 34 and the human-interface device 40 have been cleaned.

After a suitable amount of time flushing, the water stream is turned off, the cleaning device of the present disclosure 10 is removed from the human-interface device 40, and the human-interface device 40 is suitable hung such that the hose 34 and device 40 may drain out excess water and be ready for use later that evening.

The present disclosure includes that contained in the present claims as well as that of the foregoing description. Although this cleaning device of the present disclosure has been described in its preferred form with a certain degree of particularity, it is understood that the present disclosure of the preferred form has been made only by way of example and numerous changes in the details of construction and combination and arrangement of parts may be resorted to without departing from the spirit and scope of the cleaning device of the present disclosure. Accordingly, the scope of the cleaning device of the present disclosure should be determined not by the embodiment[s] illustrated, but by the appended claims and their legal equivalents.

Applicant[s] have attempted to disclose all the embodiment[s] of the cleaning device of the present disclosure that could be reasonably foreseen. It must be understood, however, that there may be unforeseeable insubstantial modifications to cleaning device of the present disclosure that remain as equivalents and thereby falling within the scope of the cleaning device of the present disclosure.

What is claimed is:

1. A human-interface cleaning device comprising:
   (a) a solvent-receiving member having a flexible base with three or more slits emanating outward from a central area of the flexible base such that the slits define an opening at the central area and further define three or more flexible flaps;
   (b) a side wall around said base, said side wall having a distal end and a proximal end, wherein said side wall extends forward of said base from the proximal end of said side wall and terminates at the distal end of said side wall;
   (c) an inner chamber defined within said side wall having a defined diameter, said inner chamber further having one or more fins extending in the direction of from the side wall's proximal end towards the side wall's distal end, wherein the one or more fins have a fin width approximately one-eighth to one-fourth of the diameter of the inner chamber; and
   (d) a solvent-discharge member at the distal end of said side wall wherein said solvent-discharge member has a tapered tubular member with a proximal end and a distal end wherein said tubular member has an opening at its said distal end, wherein said solvent-discharge member has a decreasing diameter through said solvent-discharge member, wherein said inner chamber is adapted to receive and pass a solvent through said solvent-discharge member, and wherein the tubular member is configured to be connected to a human-interface device such that solvent can pass through the tubular member and enter the human-interface device.

2. The human-interface cleaning device of claim 1 wherein said solvent-discharge member further comprises a conical member at the proximal end of said tapered tubular member, said conical member having a first end and a second end with an outside diameter at its said second end approximately equal to an outside diameter of said tubular member at the proximal end of said tubular member and further having an outside diameter at its first end which is larger than the outside diameter at its second end and is approximately equal in diameter to a diameter of the distal end of said side wall.

3. The human-interface cleaning device of claim 2 wherein said conical member is comprised of material selected from a group consisting of vinyl, rubber, polymers, and combinations thereof.

4. The human-interface cleaning device of claim 1 wherein said base is comprised of material selected from a group consisting of vinyl, rubber, polymers, and combinations thereof.

5. The human-interface cleaning device of claim 1 wherein said tubular member is comprised of material selected from a group consisting of vinyl, rubber, polymers, and combinations thereof.

6. The human-interface cleaning device of claim 1 wherein said side wall is comprised of material selected from a group consisting of vinyl, rubber, polymers, and combinations thereof.

7. The human-interface cleaning device of claim 1 wherein said distal end of said tubular member is adapted to engage by friction-fit a receiving aperture of a nasal-interface device.

8. The human-interface cleaning device of claim 1 wherein said one or more fins are approximately perpendicular to said side wall.

9. The human-interface cleaning device of claim 1 wherein said one or more fins are angled in relation to said side wall.

10. The human-interface cleaning device of claim 1 wherein said one or more fins each have an angled flap, angling curvilinearly, at its forward end.

* * * * *